(12) United States Patent
Carlino et al.

(10) Patent No.: US 7,943,750 B2
(45) Date of Patent: May 17, 2011

(54) PROCESS FOR OBTAINING PURE MONOSIALOGANGLIOSIDE GM1 FOR MEDICAL USE

(75) Inventors: Stefano Carlino, Collombey (CH); Rene-Pierre Bunter, Venthone (CH)

(73) Assignee: Laboratoire Medidom S.A., Geneva (CH)

(*) Notice: Subject to any disclaimer, the term of this patent is extended or adjusted under 35 U.S.C. 154(b) by 761 days.

(21) Appl. No.: 11/812,331

(22) Filed: Jun. 18, 2007

(65) Prior Publication Data

US 2008/0312165 A1 Dec. 18, 2008

(51) Int. Cl.
C07G 3/00 (2006.01)
C07H 17/00 (2006.01)
C07H 17/02 (2006.01)
A01N 43/04 (2006.01)
A61K 31/70 (2006.01)

(52) U.S. Cl. .................... 536/18.5; 536/17.9; 514/25

(58) Field of Classification Search .................. None
See application file for complete search history.

(56) References Cited

U.S. PATENT DOCUMENTS 4,849,413 A  7/1989  della Valle et al.
5,296,360 A  3/1994  Sugimori et al.

FOREIGN PATENT DOCUMENTS

| CA | 2002155 | 5/1990 |
|---|---|---|
| CN | 1353122 | 6/2002 |
| CN | 1379034 | 11/2002 |
| CN | 1415756 | 5/2003 |
| CN | 1814610 | 8/2006 |
| EP | 0150712 A2 | 7/1985 |
| EP | 0451270 B1 | 10/1991 |
| EP | 0469352 A1 | 2/1992 |
| EP | 0539380 B1 | 5/1993 |
| EP | 0548406 A1 * | 6/1993 |
| EP | 0816374 A2 | 1/1998 |
| EP | 0940409 B1 | 9/1999 |
| JP | 58077894 | 5/1983 |

OTHER PUBLICATIONS

Fredman et al. Biochimica et Biophysica Acta, 618 (1980) 42-52.*
Fan et al. CN1353112, Jun. 12, 2002, English abstract only.*

* cited by examiner

*Primary Examiner* — Layla Bland
(74) *Attorney, Agent, or Firm* — Baker & Daniels LLP

(57) ABSTRACT

A process for preparing pure monosialoganglioside GM1 in the form of its sodium salt. There is provided a process for the isolation and purification of monosialoganglioside GM1 comprising (a) separation of GM1 from a lipidic mixture containing the monosialoganglioside GM1 as the main ganglioside component by ion exchange column-chromatography using an eluent comprising potassium or caesium ions, (b) recovery of the solute from the eluted solution, (c) diafiltration of an aqueous solution of the recovered solute, and (d) second diafiltration after the addition of 1 M NaCl, and recovering GM1. The purity level of GM1 obtained is higher than 99.0%.

12 Claims, No Drawings

PROCESS FOR OBTAINING PURE MONOSIALOGANGLIOSIDE GM1 FOR MEDICAL USE

The present invention relates to the monosialoganglioside GM1, more particularly to processes for the obtaining and purifying the monosialoganglioside GM1.

BACKGROUND

Gangliosides are a class of glycosphingolipids, having one or more sialic acid residues, and are found abundantly in the cerebral and nervous tissue of humans and animals. The monosialoganglioside GM1 is known for a number of pharmaceutical applications, particularly in the repair and treatment of disorders of the central and peripheral nervous systems.

Gangliosides are conveniently extracted from bovine or porcine cerebral tissue according to U.S. Pat. No. 4,849,413. In order to be suitable for pharmaceutical applications, the monosialoganglioside GM1 must then be isolated and purified.

It is known to treat the extracted lipid mixture by chemical or enzymatic methods to transform other ganglioside components to the monosialoganglioside GM1, in order to increase the yield of monosialoganglioside GM1. Such methods include acid hydrolysis with a weak acid, such as described in CN 1353112, or enzymatic hydrolysis using a sialidase, for instance as described in U.S. Pat. No. 5,296,360.

Further purification of such GM1 enhanced lipidic mixture by exclusion chromatography using a chloroform:methanol:water 60:30:4.5 eluent is described in EP 0 150 712. EP 0 489 352 describes purification of a GM1 enhanced lipidic mixture by ultra-filtration of a solution of the lipidic mixture with alpha-cyclo-dextrin, followed by extraction of GM1 by solvent extraction with ethanol. It is reported that GM1 may be obtained with a purity of 95%.

Such processes have previously been shown to have drawbacks with respect to the purity and yield of GM1, and with respect to cost, efficiency and effectiveness when applied on an industrial scale.

For pharmaceutical applications it is required to produce the ganglioside GM1 at high purity. Accordingly, there remains an ongoing need for processes for obtaining the ganglioside GM1 at high-purity.

The inventors of present application have surprisingly found that the ganglioside GM1 may be effectively separated from other gangliosides by a process based on ion-exchange chromatography.

According to the present invention, it has been found that the ganglioside GM1 may be prepared at high purity by a process wherein GM1 is separated from a lipidic mixture containing the monosialoganglioside GM1 as the main ganglioside component by ion exchange column-chromatography using an eluent comprising potassium or caesium ions.

According to the present invention there is provided a process for the isolation and purification of the ganglioside GM1 according to claim 1.

According to a preferred embodiment of the present invention there is provided a process comprising the general steps of:
(a) separating GM1 from a lipidic mixture containing the monosialoganglioside GM1 as the main ganglioside component by ion exchange column-chromatography using an eluent comprising potassium or caesium ions,
(b) recovery of the solute from the eluted solution,
(c) diafiltration of an aqueous solution of the recovered solute,
(d) addition of a sodium salt and diafiltration of the resultant solution, and
(e) recovery of GM1.

Advantageously the process of the present invention allows for the preparation of the monoganglioside GM1 at high purity. According to the present invention the monosialoganglioside GM1 may be prepared with a purity of higher than 98%, even higher than 99.0% and even 99.9%.

Further, the process of the present invention advantageously uses simple steps, is cost-efficient and is suitable for application on an industrial scale.

Other objects and advantages of the present invention will be apparent from the claims and from the following detailed description and examples.

DETAILED DESCRIPTION

The present invention provides a process for the purification of the monoganglioside GM1, wherein GM1 is separated from a lipidic mixture containing the monosialoganglioside GM1 as the main ganglioside component by ion exchange column-chromatography using an eluent comprising potassium or caesium ions.

In a preferred embodiment, there is provided a process for preparing monosialoganglioside GM1 at high purity comprising the steps of;
(a) separation of GM1 from a lipidic mixture containing the monosialoganglioside GM1 as the main ganglioside component by ion exchange column-chromatography, using an eluent comprising potassium or caesium ions.
(b) recovery of the solute from the eluted solution of step (a),
(c) diafiltration of an aqueous solution of the recovered solute of step (b), in order to eliminate residual potassium or caesium salts,
(d) addition of sodium ions, preferably in the form of a suitable sodium salt, in order to displace the potassium or caesium ions bound to GM1, and diafiltration of the aqueous solution, in order to eliminate residual sodium salt, and
(e) recovery of GM1, in the form of its sodium salt.

The lipidic mixture may be prepared from crude lipid extract of bovine, ovine, equine or porcine cerebral tissue.

Advantageously, the lipidic mixture containing the monoganglioside GM1 as the prevailing ganglioside component may be prepared from a lipid extract containing at least 30%, preferably at least 50% and more preferably at least 70% of a mixture of gangliosides. The remainder of the lipid extract may generally be composed of sulfatides, cerebrosides, fatty acids and proteins.

The lipid extract may advantageously be first subjected to a diafiltration through a membrane having pore size of 10000 to 100000 Daltons, preferably about 50000 Daltons, in order to desalt the solution. For the diafiltration any conventional dialysis membrane may be used. Advantageously filter cassettes, e.g. of the SARTOCON® (Sartorius) polysulfone cassettes type may be used, for example with a cut-off of about 50000 Daltons.

Preferably the lipid extract is subject to treatment by hydrolysis to transform other major ganglioside components, such as GT1b, GD1a, and GD1b, into GM1 in order to increase the GM1 content.

The hydrolysis may be carried out using conventional methods. Advantageously the hydrolysis may be carried out using either of two general methods for hydrolysis of gangliosides known in the literature, namely acid hydrolysis or enzymatic hydrolysis.

Acid hydrolysis may be carried out, for example, using dilute mineral acid, such as dilute hydrochloric acid, sulphuric acid and nitric acid. The acid hydrolysis may be effected by adjusting the pH of an aqueous solution of the lipid extract to a pH between 3.5 and 5, preferably around pH 4.0, and heating the solution to a temperature preferably between 90° C. and 100° C. for the time necessary to complete the conversion of the other major ganglioside components to GM1. The time needed to hydrolyze the major gangliosides to GM1 depends on the pH and temperature chosen. In general, the higher the pH the longer the time required to complete the hydrolysis, and the higher the reaction temperature the shorter the time required to complete the hydrolysis. The hydrolysis reaction may generally be carried out over 2 to 5 hours. For example, where the hydrolysis is carried out at pH 4.0 and 95° C., the time required to complete the hydrolysis reaction is about 3 hours.

Enzymatic hydrolysis may be carried out using any suitable sialidase. Preferably *Arthrobacter ureafaciens* sialidase strain S or *Vibrio cholerae* sialidase may be used. Advantageously, *Arthrobacter ureafaciens* sialidase strain S and *Vibrio cholerae* sialidase are active on GT1a, GD1a, GD1b but not on GM1. Enzymatic hydrolysis may be carried out, for example, by adjusting the pH of an aqueous solution of the lipid extract to a pH at which the enzyme used has its optimum activity, for instance between pH 4 and pH 6, for example about pH 5, by adding a suitable buffer, such as acetate buffer, adding Ca2+ ions in the case that the sialidase is a *Vibrio cholerae* sialidase, and heating the solution at a temperature at which the enzyme used has its optimum activity, for example around 37° C., for the time need to complete the transformation. The hydrolysis may generally be carried out over 12-24 hours, dependant on the enzyme units added.

Acid hydrolysis is less preferred as it is a non-specific hydrolysis process and generally provides a lower yield in GM1 due to conversion to other gangliosides. Further the acid hydrolysis process leads to the formation of asialo-GM1 impurity.

The enzymatic hydrolysis methods are preferred as they generally provide a higher yield in GM1 due to the high specificity of the chemical transformation. For the enzymatic hydrolysis, *Arthrobacter ureafaciens* sialidase is preferred as it does not require the addition of Ca2+ ions for its activity. Further, due to its molecular weight of 52,000 Daltons (compared to 82,000 Daltons for *Vibrio cholerae* sialidase), it may advantageously be washed out by diafiltration.

In order to recover the thus produced lipidic mixture having an enhanced content of the monosialoganglioside GM1 from the reaction solution, the reaction solution may advantageously be diafiltered, e.g. through a membrane having pore size of 10000 to 100000 Daltons, preferably about 50000 Daltons. For the diafiltration any conventional dialysis membrane may be used. Advantageously filter cassettes, such as of the SARTOCON® (Sartorius) polysulfone cassettes type, may be used, preferably with a cut-off of 50000 Daltons. The permeate may then be dried to obtain a powder of the lipidic mixture containing the monosialoganglioside GM1 as the main ganglioside component. Drying may be carried out by conventional methods. Advantageously the drying may be carried out by spray drying or vacuum drying.

The lipidic mixture may generally have a concentration of GM1 of 10 to 200 g/lt and preferably of at least 100 g/lt.

According to the process of the present invention, the ganglioside GM1 is separated from other gangliosides in the lipidic mixture using ion-exchange chromatography.

It has surprisingly been found that where an eluent containing caesium or potassium ions is used it is possible to successfully separate out GM1 from other monosialogangliosides.

Conventionally used ion exchange techniques have generally been found not to allow effective separation of GM1 from other monosialogangliosides. Of particular note is the monosialoganglioside Fucosyl-GM1, which is present as a major ganglioside impurity in the porcine lipidic mixture produced by the known hydrolysis treatments.

The two molecules GM1 and Fucosyl-GM1 have very similar physical properties. Both have a single negative charge, provided by the carboxyl group of the sialic acid, and have similar molecular weights; 1558 and 1704 respectively. Accordingly, when loaded onto the pre-equilibrated ion-exchanger column, the binding strength of the two gangliosides with the resin is the same.

It has been observed that when sodium acetate is added to the eluent in order to increase the ionic strength of the eluent, and provide the conditions for displacement of the gangliosides, both of GM1 and Fucosyl-GM1 are eluted at the same time with the same ionic strength. No separation of the two monosialogangliosides can be achieved.

Whereas present inventors have surprisingly found that where cesium or potassium ions are used, for instance by the addition of methanolic potassium or cesium acetate, GM1 and Fucosyl-GM1 are eluted separately, with Fucosyl-GM1 being eluted first. The separation is complete, and each of the gangliosides GM1 and Fucosyl-GM1 can be isolated.

Whilst not wishing to be bound by any theory, it is considered by the inventors of the present invention, that the observed separation may be attributed to the fact that, contrary to the conventional ion-exchange theory, the solutes GM1 and Fucosyl-GM1 are not only released from the column in order of their strength in binding with the resin, but also in order of their affinity for the counter-ion to which they must bind in order to be detached from the gel. Accordingly, following this theory, if one of the two solutes has a different affinity for the counter-ion, then the solutes will be released with two different ionic strengths, and purification can occur.

It has surprisingly been found by the present inventors that the monosialogangliosides GM1 and Fuc-GM1 have the same affinity for sodium but do not have not the same affinity for potassium or caesium, despite the fact that all three metals belong to the same group. It has been found by the present inventors that Fuc-GM1 has a higher affinity for potassium and caesium than GM1, and is eluted first.

The ion-exchange chromatography method of the present invention advantageously enables effective separation of GM1 from Fucosyl-GM1. Further, the method of the present invention advantageously also allows the separation of GM1 from corresponding fatty acids. The fatty acids having the same charge as the ganglioside, but a higher affinity for caesium or potassium ions.

For the ion exchange chromatography, any suitable resin may be used. Advantageously a resin having a quaternary amino group may be used, for example, FRACTOGEL® EMD TMAE (S) or Sepharose resins e.g. Q-Sepharose HP resins.

In a first stage, the resin is equilibrated with a suitable solvent. Suitable solvents include ethanol, methanol or a mixture of methanol and chloroform. Preferably the solvent is methanol, because it is a solvent in which gangliosides and potassium and caesium salts are soluble.

The column may then be loaded with a solution of the lipidic mixture in a suitable elution solvent. The elution solvent should contain the same solvent components as the solvent used for equilibration of the resin. Preferably the solvent chosen is methanol. Preliminary elution with the elution solvent enables elution of unbound substances, e.g. cerebrosides.

Potassium or cesium ions are then added to the elution solvent. The potassium or cesium ions are preferably provided in the form of a methanolic solution of potassium or cesium acetate, formate, proprionate or as a salt of other organic acid. A methanolic solution of sodium or potassium acetate is preferred. Advantageously potassium or cesium acetate may be present in the eluent in an amount sufficient to impair a conductivity of 1100-1400 µS/cm, preferably a conductivity of 1200-1300 µS/cm on the eluent. This sodium or potassium salt containing eluent solution may be passed through the column isocratically at any suitable flow rate, for instance at a flow rate between 100 ml/h to 140 ml/h.

Where the separation is carried out using the ion exchange chromatography process according to the present invention, fatty acids and Fuc-GM1 are eluted before GM1, whilst sulfatides remain bound to the column may be eluted during column washing.

The GM1 containing eluate is collected and, advantageously, the elution solvent eluted from the column may be recovered by distillation.

The GM1 containing solute may be recovered by drying the eluate solution to produce a powder containing the GM1. Drying may be carried out using conventional methods, for instance spray-drying or vacuum drying.

The GM1 containing solute may then be purified by diafiltration of an aqueous solution thereof through a membrane having pore size of 10000 to 100000 Daltons, preferably about 50000 Daltons, in order to eliminate residual potassium or caesium salts. Optionally, a mineral acid, such as aqueous sulphuric acid, nitric acid, or preferably hydrochloric acid, may be added to the solution to adjust to a pH between pH 6 to 8, preferably about pH 7 before diafiltration.

Sodium ions, suitably in the form of an aqueous solution of a sodium salt, preferably NaCl, may then be added to the solution, in order to displace the potassium or caesium ions linked to GM1, and obtain GM1 in the form of the physiological sodium salt. The solution may then be subject to a second diafiltration in order to eliminate residual salt (e.g. NaCl), using a membrane having pore size of 10000 to 100000 Daltons, preferably about 50000 Daltons. Advantageously filter cassettes, such as cassettes of the SARTOCON® (Sartorius) polysulfone type, may be used, preferably with a cut-off of 50000 Daltons.

The solution may then be dried to recover the GM1 in the form of a powder. Drying may be carried out by conventional methods. Advantageously the drying may be carried out by spray drying or vacuum drying.

GM1 obtained according to the present invention has a degree of purity of 98% or more, generally of about 99.0 to 99.9%. The GM1 obtained according to the process of the present invention contains less than 0.1% Fucosyl-GM1 impurity.

The process of the present invention advantageously enables efficient separation of GM1 from other monosialogangliosides. Particularly, the process of the present invention allows the separation of GM1 from Fucosyl-GM1 impurity.

Advantageously the process of the present invention allows the preparation of the monosialoganglioside GM1 with a good yield and a high level of purity. Accordingly, the invention includes the purified monosialoganglioside GM1 in a pharmaceutically acceptable carrier, which pharmaceutical composition is prepared by techniques known to those skilled in the art. In one embodiment, the composition is sterile.

The purified GM1 according to the process of the present invention may be used in the treatment of human, mammal or animal subjects. Particularly, the purified GM1 according to the present invention is envisaged for the treatment of humans or mammals, particularly for the repair and treatment of disorders and diseases of the central and peripheral nervous systems, including cerebral stroke, Parkinson's disease, spinal cord injury, Alzheimer's disease, Tardive Dyskenisia, Amyotrophic Lateral Schlerosis, peripheral neuropathies and autonomic neuropathy. Preferably, a therapeutically effective amount of a pharmaceutical composition comprising the purified monosialoganglioside GM1 in a pharmaceutically acceptable carrier is administered to a patient, i.e., a human, mammal or animal in need of treatment.

The present invention is further illustrated by the following examples.

EXAMPLES

Example 1

Preparation of a Lipidic Mixture Containing the Monosialoganglioside GM1 as the Principal Ganglioside Lipid extract containing a mixture of gangliosides having a purity of 70% is dissolved in purified water at a concentration of about 25 g/l. This solution is then diafiltered through SARTOCON® (Sartorius) polysulfone filter cassettes having a cut-off of 50 000 Daltons.

200 l of the solution are then equilibrated to pH 5.5 by addition of 50 mM acetate buffer and 4 mM of Calcium chloride. 30000 U of *Vibrio cholerae* sialidase are added and the solution heated to 37° C. for 12 h to complete transformation of other major gangliosides (GT1b, GD1a, GD1b) to GM1. The resulting solution has a GM1 concentration of 14-15 g/l.

After the enzymatic hydrolysis, the solution is diafiltered through filter cassettes having a cut-off of 50 000 Daltons. 1 M NaCl is then added to the retentate and the solution subjected to a second diafiltration. After the second diafiltration the retentate is concentrated to a concentration of GM1 of 100 g/l by letting the permeate flow without any water replacement. Then, the solution is dried under vacuum to obtain about 3200 g of a powder having a GM1 concentration of 85% measured by HPLC.

Purification of GM1 from Lipidic Mixture Containing the Monosialoganglioside GM1 as the Principal Ganglioside A methanolic solution at a concentration of 10 g/l is prepared using the powder obtained in the previous step, and the solution is filtered through a 0.22 µm Sartopore cartridge filter (manufactured by Sartorius AG).

For each cycle, 7 litres of the filtered solution are then loaded on an FPLC column containing 20 l of Fractogel® EMD TMAE (S) resin equilibrated in methanol. The column is then eluted with methanol: potassium acetate methanolic solution having a conductivity of 1200-1300 µS/cm, at a flow rate of 120 l/h. The cycles repeated until the end of the GM1 solution.

The eluate (about 60-70 l) is continuously concentrated by distillation, and is then dried to obtain a powder, and methanol is recovered. The thus-obtained powder is a mixture of pure GM1 and potassium acetate.

The thus-obtained powder is dissolved in purified water to a concentration of 25 g/l, and equilibrated to pH 7 by the addition of 18% HCl. The solution is diafiltered through filter cassettes having a cut-off of 50,000 Daltons. 1M NaCl is then added and the solution is again diafiltered through filter cassettes having a cut-off of 50,000 Daltons. After this second diafiltration the retentate is concentrated up to 100-120 g/l by letting the permeate flow without any water replacement.

The concentrated solution is then filtered through a 0.22 μm filter and dried by spray drying to provide about 2700 g of a white to white-beige powder of GM1, identified by TLC, this GM1 powder having a purity of 99.8% measured by HPLC. The resultant GM1 powder has a Fuc-GM1 content of less than 0.1%, measured by HPLC.

Comparative Example

The process for preparing and purifying GM1 was carried out as in Example 1 above, except that in the column chromatography, the methanol:potassium acetate methanolic solution was replaced by a methanol:sodium acetate methanolic solution.

3100 g of a powder of GM1 was obtained containing 91% GM1 and 8% Fuc-GM1, measured by HPLC.

From the above examples it can be seen that a much lower purity of GM1 is obtained where sodium acetate is used for the elution of GM1. This may be attributed to the fact that the sodium counter-ion does not make any difference between GM1 and Fuc-GM1 in the elution process, compared with potassium or caesium counter-ions, which on the contrary completely separate both peaks.

All publications, patents, and patent applications identified above are incorporated herein by reference in their entirety.

Although this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A process for the isolation and purification of monosialoganglioside GM1 comprising the steps of:
   (a) separating GM1 from Fucosyl-GM-1 in a lipidic mixture containing the monosialoganglioside GM1 as the main ganglioside component by ion exchange column-chromatography using an eluent comprising potassium or caesium ions;
   (b) recovering the solute from the eluted solution;
   (c) diafiltrating an aqueous solution of the recovered solute of step (b);
   (d) adding a sodium salt and re-diafiltrating the resulting aqueous solution; and
   (e) collecting GM1 in the form of its sodium salt.

2. The process according to claim 1 wherein the eluent comprises potassium or caesium acetate.

3. The process according to claim 2 wherein the eluent is a methanolic solution of potassium or caesium acetate.

4. The process according to claim 1 wherein the ion-exchange column contains a resin having an amino-quaternary group.

5. The process according to claim 1 wherein the ion exchange column is first equilibrated with methanol.

6. The process according to claim 1 wherein NaCl is added in step (d).

7. The process according to claim 1 wherein the diafiltrating in step (c) and the rediafiltering in step (d) are carried out using a membrane having a pore size of 10000-100000 Daltons.

8. The process according to claim 1 wherein the recovery of GM1 in step (e) comprises drying of the permeate solution by spray drying or vacuum drying to produce a powder.

9. The process according to claim 1 comprising a preliminary purification step prior to the separation of GM1 by ion-exchange chromatography, said purification step comprising;
   (a) diafiltration of an aqueous solution of a lipidic mixture containing the monosialoganglioside GM1 as the main ganglioside component through a membrane having a pore size of 10000-100000 Daltons,
   (b) concentration of the permeate and recovery of the solute lipidic mixture comprising GM1.

10. The process according to claim 1 wherein the lipidic mixture containing the monosialoganglioside GM1 as the main ganglioside component is obtained by hydrolysis of a lipid extract containing a mixture of gangliosides having a purity of at least 50%.

11. The process according to claim 10 wherein the hydrolysis is carried out by treating the lipid extract with an *Arthrobacter ureafaciens* strain S sialidase or *Vibrio cholerae* sialidase.

12. A process for the purification of monosialoganglioside GM1 comprising separating monosialoganglioside GM1 from Fucosyl-GM-1 in a lipidic mixture containing the monosialoganglioside GM1 as the main ganglioside component, by ion exchange column-chromatography using an eluent comprising potassium or caesium ions.

* * * * *